United States Patent [19]

Tabor

[11] 3,999,541
[45] Dec. 28, 1976

[54] METHOD AND MEANS FOR COOLING INHALENT GASES

[76] Inventor: Carl J. Tabor, 2817 Park Ave., St. Louis, Mo. 63104

[22] Filed: Jan. 14, 1975

[21] Appl. No.: 540,909

[52] U.S. Cl. .................. 128/191 A; 128/212; 128/1 B
[51] Int. Cl.² .................. A61M 16/00
[58] Field of Search .......... 128/191 A, 191 R, 1 B, 128/194, 204, 142.3, 142, 142.5, 145.8, 145.6, 212

[56] References Cited
UNITED STATES PATENTS

| | | | |
|---|---|---|---|
| 1,744,890 | 1/1930 | Hanrahan | 128/191 A |
| 1,913,347 | 6/1933 | Taylor | 128/191 A |
| 2,104,589 | 1/1938 | Hartman | 128/191 A |
| 3,050,058 | 8/1962 | Andrews, Jr. | 128/191 A |
| 3,565,072 | 2/1971 | Gauthier | 128/191 A |
| 3,593,712 | 7/1971 | Weaver et al. | 128/191 A |

Primary Examiner—Robert W. Michell
Assistant Examiner—Henry J. Recla
Attorney, Agent, or Firm—John D. Pope, III

[57] ABSTRACT

A device for cooling inhalent gases including oxygen supplied to an air recirculator associated with an oxygen tent. The pre-cooled gas such as oxygen is supplied to an air recirculator such as a nebulizer unit where it is mixed with the recirculated air to replenish the oxygen content and reduce the temperature thereof.

8 Claims, 3 Drawing Figures

METHOD AND MEANS FOR COOLING INHALENT GASES

This invention relates to a method and means for cooling inhalent gases. Various forms of apparatus have been devised for cooling the recirculated inhalent gases in an oxygen tent, said cooling being desirable for the comfort of the patient whose body heat warms the recirculating air and who moreover is frequently running a temperature. These apparatus have taken several forms but have all involved cooling the recirculated air by passing it over a cooling means such as ice or refrigeration coils. They have also all suffered from the common shortcoming that they eliminate moisture from the recirculated air which tends to dry the respiratory passages of the patient. In some of the prior art devices, refrigeration coils have been located inside the oxygen tent creating problems with the elimination of water condensate therefrom. In others, the refrigeration coils have been located outside of the oxygen tent transferring the condensate problem from the oxygen tent to the refrigeration unit. Here the unit may become a breeding place for cross-infections from patient to patient since in actual hospital practice these devices are not sterilized. Furthermore, when the air is recirculated through a nebulizing unit and a medicament is added, some of the medicine may be condensed in the refrigeration unit and then later gradually revaporized, sometimes administering the medicine to an unintended patient.

Among the several objects of the present invention may be noted the provision of a method and means for pre-cooling gas such as oxygen supplied to a recirculating means associated with an oxygen tent which cooling means do not cause condensation of water vapor from the recirculated air and which do not provide a place for the growth of bacteria or the condensation of medicament. Other objects and features will be in part apparent and in part pointed out hereinafter.

The invention accordingly comprises the constructions and methods hereinafter described, the scope of the invention being indicated in the following claims.

In the accompanying drawings, in which one of various possible embodiments of the invention is illustrated, FIG. 1 is a perspective view of the refrigeration means for pre-cooling gases supplied to a recirculating means for use in inhalation therapy;

Figure 1:
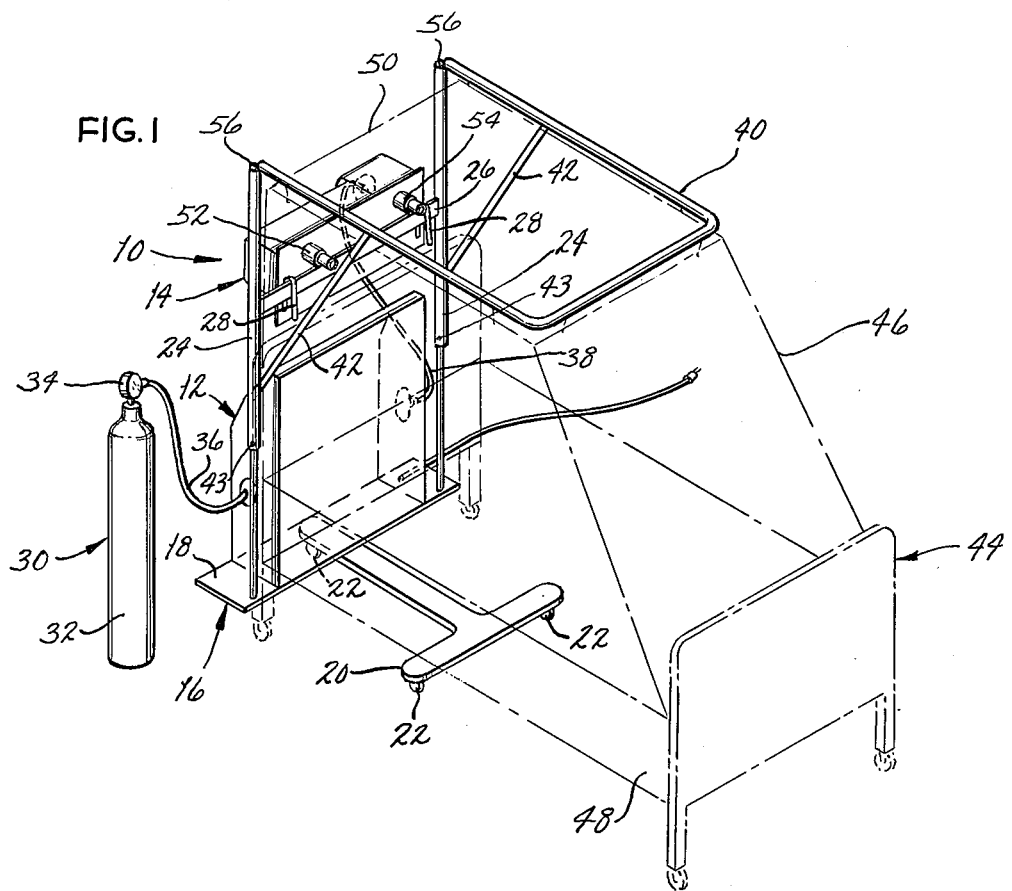

Referring to FIG. 1, an inhalation therapy unit 10 includes a refrigeration means 12 and a nebulizer 14 supported on a frame 16. The lower portion of frame 16 includes base 18 and foot 20 mounted on casters 22 and the upper portion includes telescoping upright members 24 with a cross-bar 26 therebetween. Refrigeration means 12 are mounted on base 18 and nebulizer 14 is suspended by hooks 28 to cross-bar 26. A gas supply 30, shown as including, for example, a tank 32 containing oxygen and having conventional regulators 34 for monitoring the pressure and flow of the gas therefrom, is connected by flexible tube 36 to refrigeration means 12, which in turn is flowably connected by flexible tube 38 to nebulizer 14.

A U-shaped member 40 is the canopy support which is connected at the upper ends of upright frame members 24. Braces 42 further connect upright members 24 and canopy support 40. The length of telescoping upright members 24 may be adjusted at pins 43 so that the height of the canopy support may be adjusted for the type of bed 44, shown in broken lines. Suspended on canopy support 40 is oxygen tent or canopy 46, also shown in broken lines, preferably constructed of some clear plastic material, and tucked at its lower edges under mattress 48. Canopy 46 is connected through wall 50 by sleeves 52 and 54 to nebulizer 14.

When inhalation therapy unit 10 is not in use, canopy 46 may be removed from canopy support 40 and braces 42 released, the canopy support may then be folded at hinges 56 against upright members 24 for transport and storage after being disconnected from oxygen supply 30. Nebulizer 14 may be easily removed by unhooking it from cross-bar 26 for cold or gas sterilization with plastic oxygen tent 46. When the unit is needed again it is easily transported on casters 22, quickly unfolded and reassembled in sterile condition.

Figure 2:
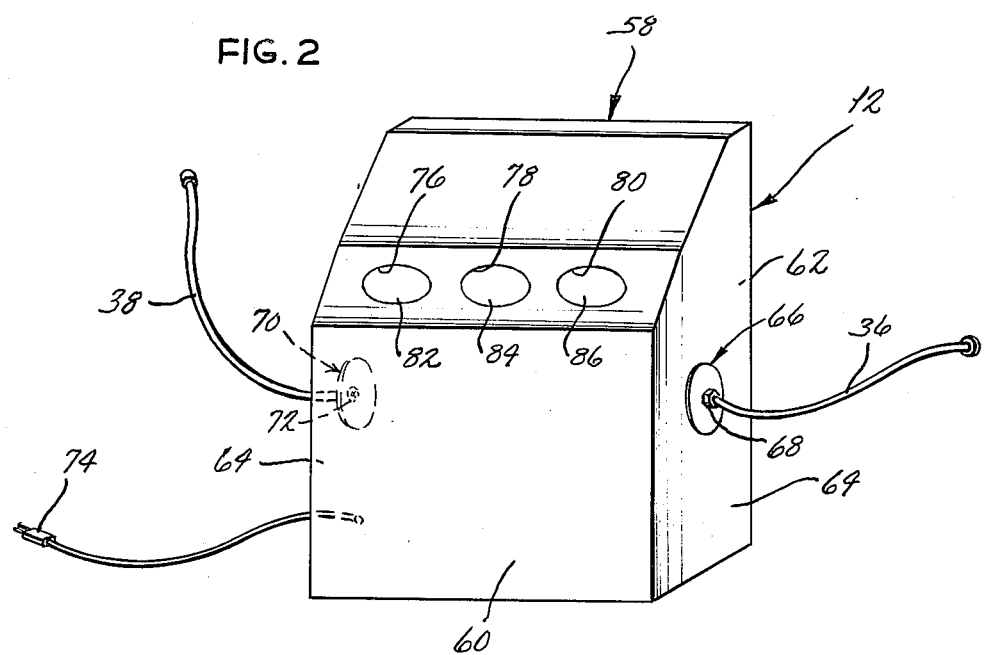
FIG. 2 is an enlarged perspective view of the refrigeration means.

As best seen in FIG. 2, refrigeration means 12 are housed in a control cabinet 58 with front 60, back 62 and end panels 64 dimensioned so that the cabinet is thin front to back to conserve space. Right end 64, as viewed in FIG. 2, has an inlet 66 with a threaded fitting 68 for coupling with flexible tube 36 connected to gas supply 30 and left end 64 is provided with an exit 70 with a similar threaded fitting 72 for coupling with flexible tube 38 connected to nebulizer 14. The cabinet is further provided with an electrical connector 74 and with apertures 76, 78 and 80 for switch 82, gauge 84 and thermostat control 86, respectively. Switch 82 comprises a toggle switch with an on/off pilot light (not shown) while gauge 84 includes a temperature indicator which is responsive to settings of thermostat control 86, as described hereinafter.

Figure 3:
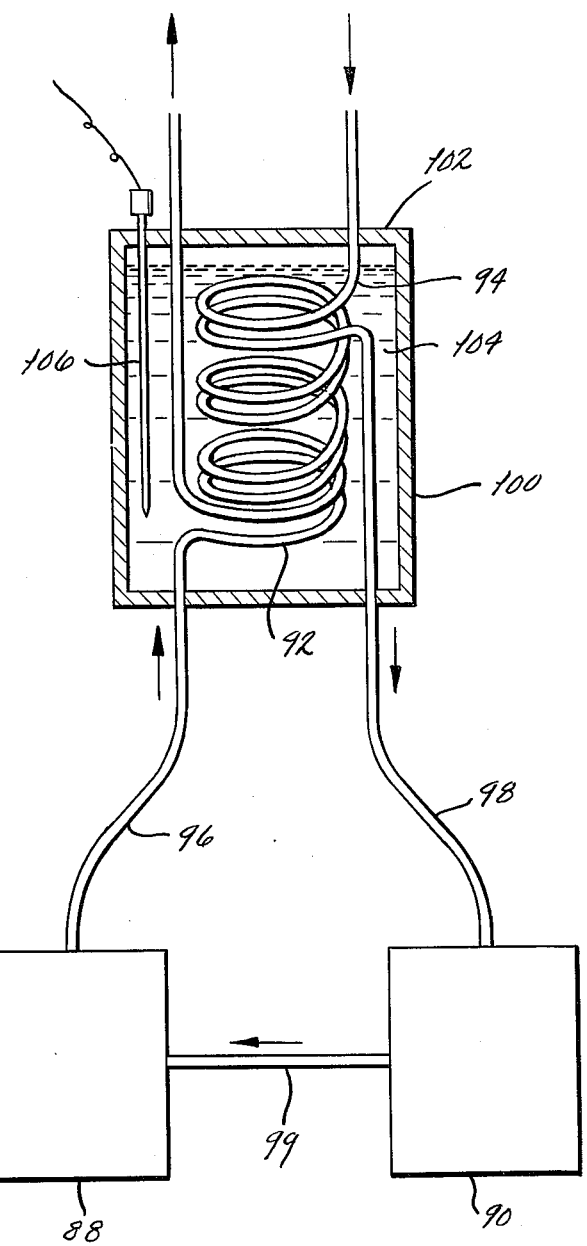
FIG. 3 is a schematic view of the refrigeration means.

The refrigeration means, as shown schematically in FIG. 3 are located inside control cabinet 58. In addition to a conventional compressor 88 and a condenser 90, refrigeration means 12 include refrigeration coils 92 which are in heat exchange relationship with heat exchange coils 94. Heat exchange coils 94 pre-cool the gas supplied from gas supply 30 passing through inlet 66 en route to nebulizer 14 passing through exit 70 in the direction of the arrows, as shown in FIG. 3, and described below. Refrigeration coils 92 are cooled in a conventional manner by means of a cooled refrigerant such as Freon which is caused to be recycled in the direction of the arrows, as shown in FIG. 3, through refrigeration coils 92 from compressor 88 through tube 96 and then to condenser 90 through tube 98 and back to compressor 88 through tube 99. Refrigeration coils 92 and heat exchange coils 94 are constructed of some thermally conductive material such as copper and are located in an insulated container 100 which is provided with a tight fitting insulated cover 102. To facilitate heat exchange between refrigeration coils 92 and heat exchange coils 94, insulated container 100 is nearly filled with a heat exchange fluid 104 such as ethylene glycol. The temperature of this fluid is monitored by a temperature probe 106 shown as penetrating through insulated cover 102 to a midpoint in heat exchange fluid 104. Temperature probe 106 is connected to temperature gauge 84 on control cabinet 58.

In operation, with the unit plugged in by means of electrical connector 74 and on/off switch 82 turned on, the refrigeration cycle takes place until temperature probe 106 indicates a temperature on temperature control gauge 84 which is the temperature preselected on thermostat control 86. Gas flowing from supply source 30 through inlet 66 enters the upper coil of heat exchange coils 94, as shown in FIG. 3. As the gas passes through the coils, the gas is cooled by heat exchange fluid 104 which is gradually warmed. When the fluid has warmed to the preselected temperature on thermostat control 86 as monitored by temperature probe 106, the refrigeration cycle is then reactivated until the preselected temperature is again reached.

According to the method of the present invention, the pre-cooled gas such as oxygen passing through exit 70 and through tube 38 to nebulizer 14 is mixed in the nebulizer with recirculated air which enters the nebulizer through sleeve 52 and which may be pretreated in the nebulizer if desired with soda lime to remove carbon dioxide. After the recirculated air is mixed with the pre-cooled gas flowing from refrigeration means 12, it is replenished in oxygen and is cooled in temperature. No water is found to condense in the nebulizer unit since the dew point of the water vapor is never reached and hence no moisture is removed from the recirculated air. The cooled, oxygen replenished air is then passed through sleeve 54 back into oxygen tent 46.

The temperature of the recirculated air within canopy 46 is monitored by a temperature gauge (not shown) associated with nebulizer 14 or which is hung in the oxyen tent. Manual adjustments of thermostat control 86 on control cabinet 58 effect control of the temperature of the gas entering nebulizer 14 and thusly of the recirculated air in the oxygen tent. As will be readily apparent, the desired temperature setting for thermostat control 86 will depend on the flow rate of the gas through heat exchange coils 94, said amount usually being between 5 to 15 liters per minute as directed by the physician, since the temperature of the heat transfer fluid must vary inversely with the flow rate of the gas to obtain a particular degree of cooling. Indicia are provided (not shown) on control cabinet 58 correlating control thermostat readings and gas flow rates with desired temperatures of the recirculating air in the oxygen tent.

In view of the above, it will be seen that the several objects of the invention are achieved and other advantageous results attained.

As various changes could be made in the above constructions and methods without departing from the scope of the invention, it is intended that all matter contained in the above description or shown in the accompanying drawings shall be interpreted as illustrative and not in a limiting sense.

What is claimed is:

1. A breathing therapy apparatus including a respiration chamber and a nebulizer flowably connected to the atmosphere in the respiration chamber and flowably connected to a supply of make-up respirable gas, and means for pre-cooling the make-up respirable gas flowed into the nebulizer, wherein said nebulizer has first and second inlets and an outlet, a first passageway connected to the respiration chamber and the first inlet of the nebulizer, a second passageway connected to said means for pre-cooling the make-up respirable gas and to the second inlet of the nebulizer, said second inlet being in downstream flow relationship to the first inlet, and a third passageway connected to the outlet and the respiration chamber.

2. A breathing therapy apparatus according to claim 1 further comprising a carbon dioxide removing means interposed between the first inlet and the outlet in the nebulizer so that the recirculated atmosphere from the respiration chamber is circulated thereover before it is recirculated to the respiration chamber.

3. A breathing therapy apparatus according to claim 2 wherein a refrigeration means is interposed in the second passageway.

4. A breathing therapy apparatus according to claim 3 wherein a thermally conductive tube is interposed in the second passageway and wherein the refrigeration means includes a refrigeration coil in heat exchange relationship with the conductive tube.

5. A method for cooling inhalent gases in a breathing therapy apparatus comprising recirculating breathed gas between a respiration chamber and a nebulizer, providing a flow of make-up respirable gas into said nebulizer, pre-cooling said make-up respirable gas flowed into said nebulizer, mixing the pre-cooled respirable gas with the recirculated atmosphere in the nebulizer and recirculating the gas mixture into the respiration chamber.

6. The method for cooling inhalent gases according to claim 5 wherein the recirculated atmosphere in the air recirculating means is first passed over a means for eliminating the carbon dioxide before it is recirculated to the respiration chamber.

7. The method for cooling inhalent gases according to claim 6 wherein the respirable gas is cooled by passing it through a thermally conductive tube which is cooled by refrigeration means.

8. The method for cooling inhalent gases according to claim 7 wherein the thermally conductive tube is cooled by a heat transfer fluid which is in heat transfer relationship with the refrigeration means.

* * * * *